(12) United States Patent
Leconte

(10) Patent No.: US 9,658,057 B2
(45) Date of Patent: May 23, 2017

(54) FACILITY FOR MEASURING THE THICKNESS OF THE WALL OF CONTAINERS

(71) Applicant: MSC & SGCC, Vourles (FR)

(72) Inventor: Marc Leconte, Loire sur Rhone (FR)

(73) Assignee: MSC & SGCC, Vourles (FR)

( * ) Notice: Subject to any disclaimer, the term of this patent is extended or adjusted under 35 U.S.C. 154(b) by 0 days.

(21) Appl. No.: 14/434,780

(22) PCT Filed: Oct. 18, 2013

(86) PCT No.: PCT/FR2013/052490
§ 371 (c)(1),
(2) Date: Apr. 10, 2015

(87) PCT Pub. No.: WO2014/060707
PCT Pub. Date: Apr. 24, 2014

(65) Prior Publication Data
US 2015/0276380 A1 Oct. 1, 2015

(30) Foreign Application Priority Data
Oct. 18, 2012 (FR) ...................................... 12 59940

(51) Int. Cl.
*G01B 11/06* (2006.01)
*G01N 21/90* (2006.01)

(52) U.S. Cl.
CPC ............. *G01B 11/06* (2013.01); *G01N 21/90* (2013.01)

(58) Field of Classification Search
CPC ...................................................... G01B 11/06
See application file for complete search history.

(56) References Cited

U.S. PATENT DOCUMENTS

| 4,822,171 | A | 4/1989 | Brand et al. |
| 7,385,174 | B2 * | 6/2008 | Ringlien ................ G01B 11/06 209/524 |
| 2004/0027579 | A1 * | 2/2004 | Lee ........................ G01B 11/06 356/504 |

FOREIGN PATENT DOCUMENTS

| EP | 0 320 139 | | 6/1989 |
| FR | 2 069 220 | | 9/1971 |
| GB | 1329240 A | * | 9/1973 |
| WO | 2012/110749 | | 8/2012 |

* cited by examiner

Primary Examiner — Kara E Geisel
Assistant Examiner — Shawn Decenzo
(74) Attorney, Agent, or Firm — Clark & Brody

(57) ABSTRACT

A facility for measuring the thickness of the wall of containers includes an optical system for collecting and focusing on the detection plane of a light sensor and light beams reflected by the outer and inner surfaces of the wall. An optical collecting and focusing system includes a first objective having is object plane located in the vicinity of the impact of the incident light beam with the wall, an at least translucent diffusing screen located in the image plane of the first objective, so as to physically represent the light beams collected by the first objective as hot spots (Ti), and a second objective including, the diffusing screen as an object plane and the light sensor as an image plane.

8 Claims, 3 Drawing Sheets

FACILITY FOR MEASURING THE THICKNESS OF THE WALL OF CONTAINERS

FIELD OF THE INVENTION

The present invention relates to the technical field of optoelectronic inspection of containers of transparent or translucent nature, such as bottles, pots, or flasks with view to detecting material distribution defects and in particular thickness defects usually called defects of the thin type.

BACKGROUND OF THE INVENTION

In the technical field for making glass containers, it is known that there exists a risk that the containers have one or several localized areas with poor distribution of the material affecting the esthetics or more seriously the mechanical strength of the containers. It is known that small thickness or "thin" defects mainly form in specific regions of the container which have different radii of curvature such as the shoulder or the chime of the container.

In order to measure the thickness of the wall of a bottle, a so-called triangulation method is known, consisting of projecting a light beam onto the wall of the article with a non-zero angle of incidence, and of collecting the light beams reflected by the outer surface and the inner surface of the wall. These light reflections on both of these surfaces occur according to the laws of specular reflection of the incident beams, i.e. symmetrically to the incident beam relatively to the normal to the surface at the impact point of the incident beam.

Measurement of the thickness of the container 2 is for example known from patent EP 0 320 139 and as illustrated in FIG. 1, by sending a light beam B onto the wall of the container with an angle such that a portion C of the light beam is reflected by the outer surface of the wall and that a portion of the beam is refracted in the wall and then reflected D by the inner surface of the wall. The rays C, D reflected by the inner and outer surfaces of the wall are collected by a lens E in order to be sent on a linear light sensor F. The plane containing the optical axis, the linear sensor and the median radius of the incident beam is currently called the triangulation plane. The thickness of the wall of the container is measured depending on the separation, at the light sensor, between the beams reflected by the inner and outer surfaces of the wall. The container is driven into rotation so as to perform one revolution in order to measure its thickness along one of the transverse cross-sections. Advantageously, the inspection cross-section is located in an area of the container having a great risk of forming thin areas such as the chime or the shoulder.

An alternative to the previous technique consists of using an array sensor instead of a linear sensor in order to measure the glass thickness and therefore its distribution around the whole of the height of the resulting field covered by the array sensor provided with an objective. In this configuration, the light beam produced by the source extends perpendicularly to the triangulation plane so as to vertically cover the field of the array sensor.

Because of the geometrical shape of the container to be monitored and/or because of the lack of parallelism between the inner and outer surfaces of the wall to be measured, the deviations of the directions of both specular reflections may vary by several degrees. Thus, as illustrated in FIG. 1, the geometrical shape of the article may cause significant variation of the position of the impact point of the incident beam so that the reflected rays C', D', may have strong deviations relatively to the optical axis and the points from which they stem may have a large position deviation. Also, as illustrated in FIG. 1A, the lack of parallelism between the inner and outer surfaces of the wall to be measured may lead to reflected rays C", D" having strong deviations relatively to the optical axis.

A method for measuring the thickness of an object is also known from patent FR 2 069 220, consisting of projecting a narrow light beam onto the object so that the light beam successively produces a spot of light on the external face and the internal face of the object. A lens is positioned relatively to the object in order to form real images of the light directly reflected or diffusively reflected by the inner and outer surfaces, like two concentrated light points spaced apart on a screen. The distance between both of these spots is measured with any device such as for example, a vidicon or an image analyzer.

According to a preferred alternative embodiment, the lens is positioned so as not to receive the light rays which are directly reflected by the inner and outer surfaces according to angles equal to the angles of incidence on these surfaces. This technique, which intends to form real images of the diffusively reflective light, cannot be notably applied for monitoring the thickness of the walls of bottles since the light is not reflected on the walls in a diffusive way.

However this patent provides the case when the lens is provided for collecting a directly reflected ray. This patent however specifies that in such a case, a small change in the surface angle of the object changes the angle of the reflected ray, requiring significant motion of the lens for collecting this reflected ray.

The technique described in this patent is not industrially applicable as it is inconceivable to move the lens for collecting the reflected rays.

Therefore appears the need for being able to have a facility for measuring the thickness of the wall of transparent or translucent containers operating for a wide range of containers and/or under significant deviation conditions of the beams reflected by the wall and/or under significant position deviation conditions of both reflection points.

However, in the field of the design of focusing optics such as objectives, it is known that extreme conditions, notably collecting rays forming a large angle with the optical axis and/or stemming from points of the object plane away from the optical axis, or else large incidences on the image sensors, lead to optical aberrations and light losses, which are detrimental to the operation of the sensor and of the objective or else are costly and complex to correct.

The present invention aims at finding a remedy to the drawbacks of the prior art by proposing a performing and economical facility for measuring the thickness of the wall of transparent or translucent containers, operating for a wide range of containers and/or under significant deviation conditions of the beams reflected by the war and/or significant position deviation conditions of both reflection points.

SUMMARY OF THE INVENTION

In order to achieve such a goal, the facility for measuring the thickness of the wall of transparent or translucent containers, delimited between an outer surface and an inner surface, includes:
 a light source producing a light beam sent in order to impinge the outer surface of the wall according to an incident angle such that a portion of the light beam is reflected by the outer surface of the wall and that a portion of the beam is refracted in the wall and then reflected by the inner surface of the wall, a dimensioned light sensor, placed in a detection plane, and collecting the light in order to convert it into electric signals, an optical system for collecting and focusing on the detection plane of the light sensor, light beams reflected by the outer and inner surfaces of the wall, a processing unit connected to the light sensor and adapted in order to determine the thickness of the wall from the electric signals delivered by the light sensor.

According to the invention, the optical collecting and focusing system includes, successively positioned on the optical axis in the direction of propagation of the beams reflected by both surfaces:

a first objective having its object plane located in the vicinity of the impact of the incident light beam with the wall and adapted for collecting the light beams specularly reflected by the outer and inner surfaces of the wall, an at least translucent diffusing screen located in the image plane of the first objective, so as to physically represent the light beams collected by the first objective as hot spots, a second objective having in its object plane, the diffusing screen and in its image plane, the light sensor, so as to produce on the light sensor, an image of the diffusing screen in which hot spots are distinguished.

Further, the facility according to the invention may further include as a combination, at least either one or/and both of the following additional features:

the optical collecting and focusing system combines a dimensioned object field with the dimensioned light sensor so that Ci<0.5 Co and transmits up to the light sensor an incoming ray with an angle relatively to the optical axis of less than 40°, the first objective combines the wall and the diffusing screen with a magnification of more than 1 and preferably about 1.5, and is capable of collecting and focusing on the diffusing screen, rays entering its pupil with an angle relatively to the optical axis which may attain at least 20° and may range up to 40°, the screen is diffusive in its bulk or at its surface, the diffusive power being adapted so that the scattered rays are collected by the second objective, the light source produces an elongated beam perpendicularly to the triangulation plane and narrow in the orthogonal direction, the light sensor is a linear image sensor preferably perpendicular to the optical axis of the optical collecting and focusing system, and located in the triangulation plane, or an image array sensor preferably located perpendicularly to the optical axis, the processing unit is able to determine, in the image produced by the light sensor, the position of the spots produced by both light beams illuminating the diffusing screen, and to infer their separation, the thickness of the wall in at least one section of the container.

BRIEF DESCRIPTION OF THE DRAWINGS

Various other features will become apparent from the description made below with reference to the appended drawings which show as non-limiting examples, embodiments of the object of the invention.

DETAILED DESCRIPTION OF THE INVENTION

Figure 1:
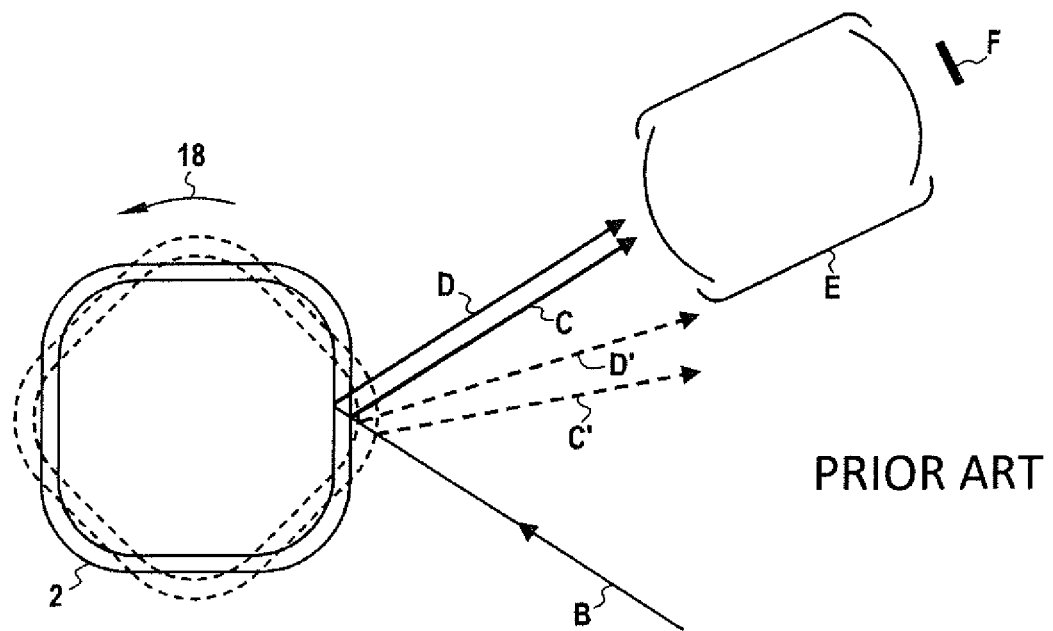
FIG. 1 is a schematic view illustrating the drawbacks of a facility according to the prior art.
Figure 1A:
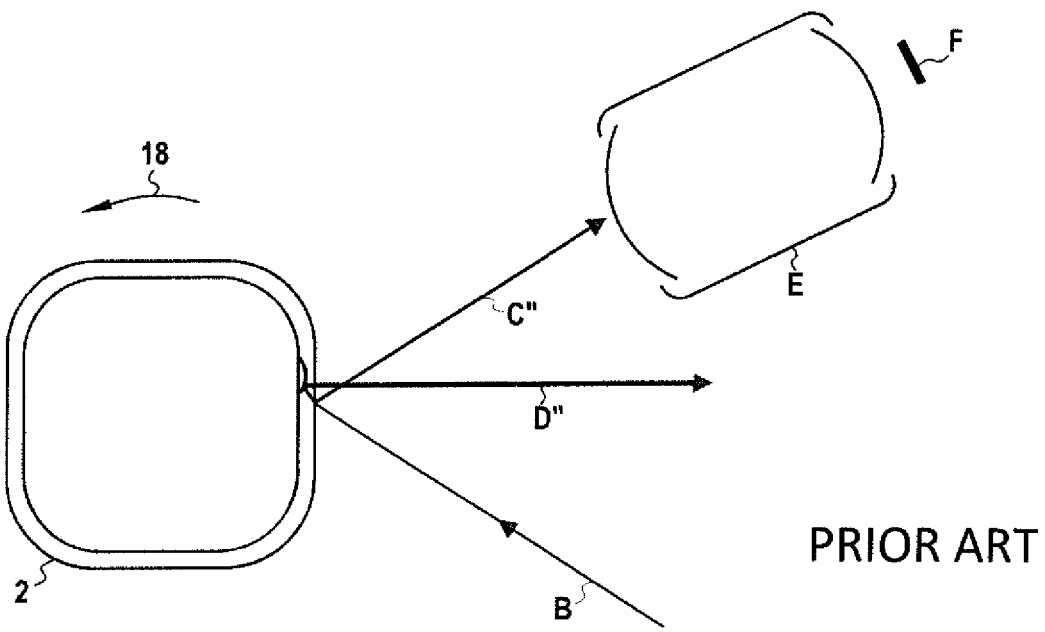
FIG. 1A is a schematic view illustrating the drawbacks of a facility according to the prior art for measuring the thickness of an object for which the walls are not parallel.
Figure 2:
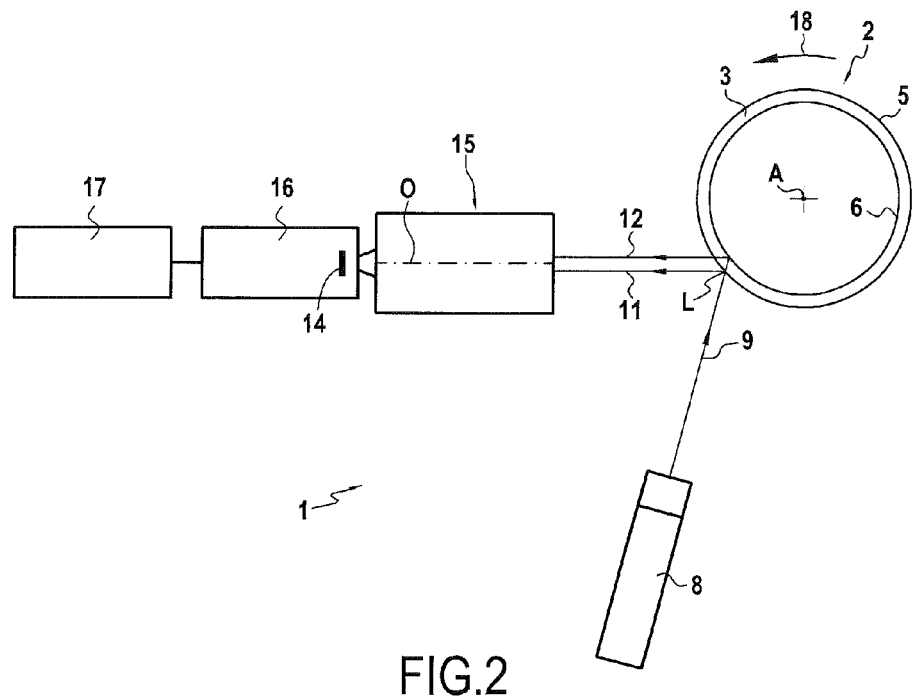
FIG. 2 is a view schematically showing a facility according to the invention for measuring the wall of a container illustrated as a section.

FIG. 2 schematically illustrates a facility 1 with which defects in the distribution of material on transparent or translucent containers 2 having a central axis A may be detected. As this more specifically emerges from FIG. 2, each container 2 has a delimited vertical wall 3 and between an outer surface 5 and an inner surface 6.

According to the invention, the facility 1 is adapted for measuring the thickness of the wall 3 of containers 2 such as glass containers, for example bottles, pots or flasks.

Advantageously, the facility 1 is adapted so as to observe an inspection area or region extending over the whole circumference of the container and having a height taken along the central axis A encompassing the area in which a material distribution defect may appear. For example, the inspection region corresponds to the chime or to the shoulder of the container.

The facility 1 includes a light source 8 adapted for sending a light beam 9 onto the wall 3 of the container, as a line of light L having a determined length according to the height of the container taken along the central axis A. for example, the light source 8 is a laser. In the case when the inspection region is a two-dimensional surface, the length of the line of light L taken along the central axis A axis corresponds to the height of the inspection region.

The light beam 9 is sent according to an angle such that a portion 11 of the light beam 9 is reflected by the outer surface 5 and that a portion 12 of the beam 9 is refracted in the wall 3 and then reflected by the inner surface 6 of the wall. As this more specifically emerges from FIG. 2, sending of the light beam 9 leads to obtaining a beam 11 reflected by the outer surface 5 and a beam 12 reflected by the inner surface 6.

The facility also includes a light sensor 14 capable of collecting, by means of an optical collecting and focusing system 15, the beams 11, 12 specularly reflected by the outer 5 and inner 6 surfaces respectively. It is recalled that a reflection is said to be specular when the radiation 11, 12 reflected by the surface is reflected along a single and same direction according to Snell's laws, i.e. the reflected beam is symmetrical to the incident beam relatively to the normal. In other words, the angle of incidence between the incident beam and the normal to the surface is equal to the reflection angle defined between the reflected beam and the normal to the surface. The optical collecting and focusing system 15 which will be described in more detail in the continuation of the description includes an optical axis O contained in the triangulation plane also containing the median radius of the incident light beam 9. The light sensor 14 is either a linear image sensor preferably but not exclusively perpendicular to the optical axis O of the optical collecting and focusing system 15, while being located in the plane of triangulation, or an image array sensor preferably but not exclusively located perpendicularly to the optical axis O. The light sensor 14 which is part of a linear or array camera 16 converts the light into electric signals.

The camera 16 is connected to an acquisition and processing unit 17 allowing the images taken by the light sensor 14 to be acquired and processed. The camera 16 and the acquisition and processing unit 17 are not described more specifically here since they are well known to one skilled in the art.

The inspection facility 1 also includes a system 18 for setting into rotation the containers 2 around the central axis A over one revolution so as to allow inspection of the containers along the whole of its circumference, by taking successive images during rotation of the containers.

Figure 3:
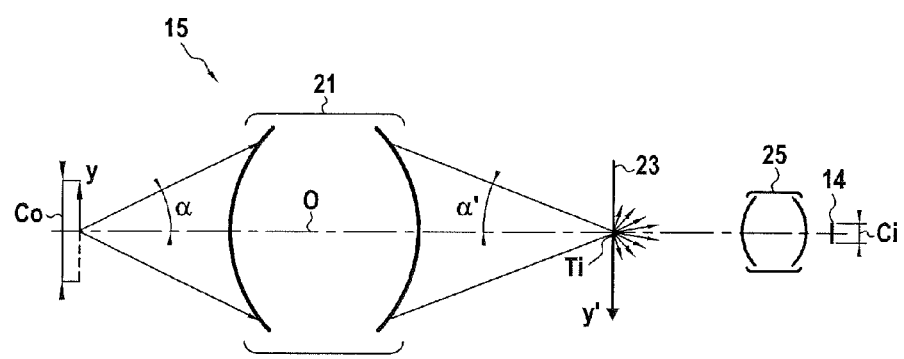
FIG. 3 illustrates the optical principle of the optical system for collecting and focusing the beams, as applied in the facility illustrated in FIG. 2.

FIG. 3 illustrates an exemplary embodiment of the optical collecting and focusing system 15. The optical collecting and focusing system 15 combines an object field Co of dimension 2.y with a light source 14 so that the light sensor has a dimension Ci of less than 0.5 times the dimension of the object field, i.e. $C_i < 0.5 \cdot Co$. The optical collecting and focusing system 15 includes:
- a first objective 21 having its object plane located in the vicinity of the impact of the incident light beam 9 with the wall 3 and adapted for collecting the light beams reflected by the outer 5 and inner 6 surfaces of the wall,
- an at least translucent diffusing screen 23 located in the image plane of the first objective 21, so as to physically represent the light beams collected by the first objective 21, as hot spots Ti,
- and a second objective 25 including as an object plane, the diffusing screen 23 and as an image plane, the light sensor 14, so as to produce on the light sensor an image of the diffusing screen 23 in which hot spots are distinguished.

The first objective 21, the diffusing screen 23 and the second objective 25 are positioned on the optical axis O successively in the direction of propagation of the beams reflected by both surfaces 5, 6.

The first objective 21 combines the wall 3 of the container 2 and the diffusing screen 23 with a magnification greater than 1 and preferably around 1.5.

The first objective 21 collects and focuses on the diffusing screen 23, rays entering its input pupil with an angle α relatively to the optical axis O which may attain at least 20° and which may range up to 40°. The first objective 21 thus collects the beams 11, 12 reflected by the outer 5 and inner 6 surfaces.

The diffusing screen 23 physically represents the light beams which arrive in the image plane of the first objective 21. In other words, the light beams intercepted by the diffusing screen 23 are either scattered in its bulk or at the surface by one of its surfaces. The light beams collected by the diffusing screen 23 are thus physically represented as hot spots Ti. The light after having crossed the diffusing screen 23 propagates according to an emission lobe which depends on the diffusive power of the screen 23. The scattering characteristics of the screen 23 are selected so that the light is in particular scattered along the direction of the light sensor 14. Thus, by observing the diffusing screen 23 from the side opposite to the incidence of the beams, it is possible to observe the thereby formed hot spots under angles related to the emission lobe.

The second objective 25 gives the possibility of again picking up the hot spots formed on the screen and of forming images of them on the light sensor 14. In this respect, the object plane of the second objective 25 is the diffusing screen 23 while its image plane corresponds to the detection plane of the image sensor 14.

As this is apparent from the foregoing description, with the optical collecting and focusing system 15 it is possible to obtain a large field of observation and a significant aperture angle. Thus, the optical collecting and focusing system 15 transmits as far as the light sensor 14, an incoming ray with an angle relatively to the optical axis O which may range up to 40° while combining an object field for which the side dimensions are at least twice the side dimensions of the light sensor 14.

Figure 4:
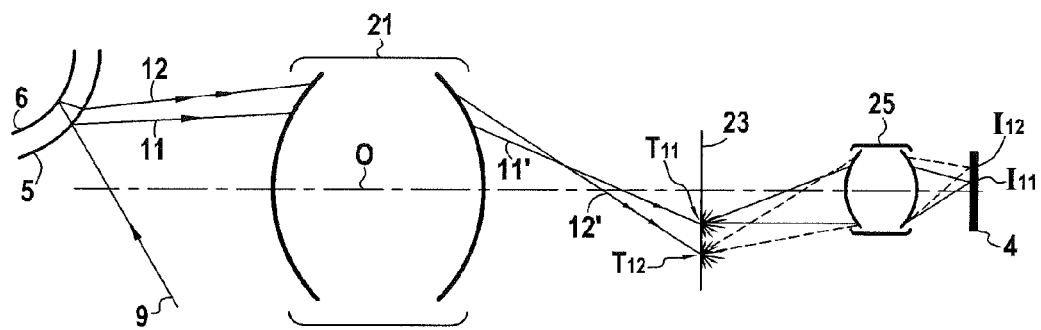
FIG. 4 illustrates an example of the travel of light beams in the optical system for collecting and focusing the beams, illustrated in FIG. 3.

FIG. 4 allows illustration of the travel of the light beams reflected by the wall 3 as far as the light sensor 14. The first objective 21 gives the possibility of collecting the rays 11, 12 reflected by the outer 5 and inner 6 surfaces respectively and of transmitting them so that the outgoing rays 11', 12' respectively form on the diffusing screen hot spots $T_{11}$, $T_{12}$.

The thereby formed image on the diffusing screen 23 and including the hot spots $T_{11}$, $T_{12}$ is taken again in order to form an image by means of the second objective 25, on the light sensor 14.

Figure 5:
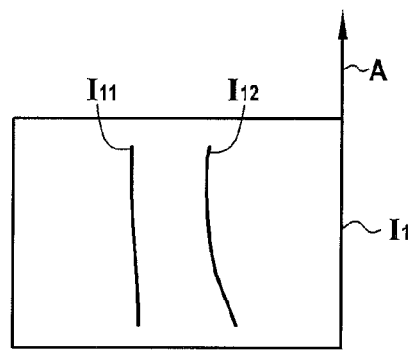
FIG. 5 is an example of an image obtained by the measurement facility according to the invention.

FIG. 5 illustrates an example of an image $I_1$ taken by the camera 16 for a determined angular position of the container 2 relatively to the light sensor 14 which, in the illustrated example, is of the array type. The image $I_1$ shows the image $I_{11}$ of the hot spot $T_{11}$ resulting from the physical representation of the reflected ray 11 on the outer surface 5 on the one hand and the image $I_{12}$ of the hot spot $T_{12}$ resulting from the physical representation of the reflected beam 12 on the inner surface 6 on the other hand. The images $I_{11}$, $I_{12}$ of the hot spots $T_{11}$, $T_{12}$ appear on the image $I_1$ along two lines of light having a length along the central axis A corresponding to the height of the inspection region of the container and are found spaced apart from each other, along a direction perpendicular to the axis A, by a distance corresponding to the thickness of the wall 3. It should be noted that in the case of a linear light sensor, the images $I_{11}$, $I_{12}$ of the hot spots appear as two points of light separated by a value corresponding to the thickness of the wall 3.

The acquisition and processing unit 17 is adapted so as to take successive images of the wall 3 of the container 2 upon rotation of the container 2 by one revolution. In other words, the acquisition and processing unit 17 takes 2 successive images for a determined rotational step, for example of the order of 1 mm according to the circumference of the container 2. Conventionally, the acquisition and processing unit 17 processes the thickness measurements by seeking whether one of the thickness measurements is less than a critical minimum thickness value. In the case when at least one thickness measurement is less than the critical minimum thickness value, the acquisition and processing unit 17 delivers a defect signal allowing the container to be reported as defective.

The invention is not limited to the described and illustrated examples since various modifications may be made thereto without departing from its scope.

The invention claimed is:

1. A facility for measuring the thickness of the wall of transparent or translucent containers, delimited between an outer surface and an inner surface, including:
   a light source producing a light beam sent to impinge the outer surface of the wall according to an angle of incidence such that a portion of the light beam is reflected by the outer surface of the wall and that a portion of the beam is refracted in the wall and then reflected by the inner surface of the wall, a light sensor of dimension Ci, placed on a detection plane, and collecting the light for converting it into electric signals, an optical collecting and focusing system, on the detection plane of the light sensor, for collecting and focusing light beams reflected on the outer and inner surfaces of the wall, a processing unit connected to the light sensor and adapted for determining the thickness of the wall from electric signals delivered by the light sensor, characterized in that the optical collecting and focusing system combines an object field of dimension Co with the light sensor (14) of dimension Ci so that Ci<0.5 Co and successively includes, positioned on the optical axis O in a propagation direction, beams reflected by both inner and outer surfaces:

a first objective having the first objective's object plane located in the vicinity of the impact of the incident light beam with the wall and adapted for collecting the light beams specularly reflected by the outer and inner surfaces of the wall, with an angle ($\alpha$) relatively to the optical axis O ranging from at least 20° to up to 40°, an at least translucent diffusing screen located in the image plane of the first objective, so as to physically represent the light beams collected by the first objective as hot spots (Ti), a second objective having in the second objective's object plane, the diffusing screen and in the second objective's image plane, the light sensor, so as to produce on the light sensor, an image of the diffusing screen on which the hot spots are distinguished.

2. The facility according to claim 1, characterized in that the first objective combines the wall and the diffusing screen with a magnification of more than 1.

3. The facility according to claim 2, wherein the magnification is around 1.5.

4. The facility according to claim 1, characterized in that the screen is diffusive in the screen's bulk or at the screen's surface, the scattering being adapted so that the scattered rays are collected by the second objective.

5. The facility according to claim 1, characterized in that the light source produces a beam perpendicularly elongated to a triangulation plane and narrow in an orthogonal direction.

6. The facility according to claim 1, characterized in that the light sensor is either a linear image sensor.

7. The facility according to claim 6, wherein the linear image sensor is perpendicular to the optical axis O of the optical collecting and focusing system, and located in the triangulation plane or the image array sensor is located perpendicularly to the optical axis O.

8. The facility according to claim 1, characterized in that the processing unit is able to determine, in the image produced by the light sensor, the position of spots produced by both light beams illuminating the diffusing screen, and to infer from the spot's separation, the thickness of the wall in at least one section of the container.

\* \* \* \* \*